United States Patent [19]

O'Donnell, Jr.

[11] Patent Number: 6,083,161
[45] Date of Patent: Jul. 4, 2000

[54] APPARATUS AND METHOD FOR IMPROVED INTRAOCULAR PRESSURE DETERMINATION

[76] Inventor: Francis E. O'Donnell, Jr., 709 The Hamptons La., Town & Country, Mo. 63017

[21] Appl. No.: 09/170,916

[22] Filed: Oct. 13, 1998

[51] Int. Cl.[7] .................................................. A61B 3/16
[52] U.S. Cl. ........................................ 600/405; 600/558
[58] Field of Search .................................. 600/405, 558, 600/398, 437, 438

[56] References Cited

U.S. PATENT DOCUMENTS 5,636,635  6/1997  Massie et al. .......................... 600/405

OTHER PUBLICATIONS

Tonometry, by Richard F. Brubaker, vol. 3, Chapter 7, Duane's Clinical Opthalmology, 1996.

*Primary Examiner*—Cary O'Connor
*Assistant Examiner*—Pamela Wingood
*Attorney, Agent, or Firm*—Paul M. Denk

[57] ABSTRACT

A novel apparatus and method of intraocular pressure determination is disclosed in which applanation tonometery is done with an ultrasonic transducer. The method allows for increased accuracy of intraocular pressure determination based upon adjustment of applanation tonometry for subjacent corneal thickness.

8 Claims, 2 Drawing Sheets

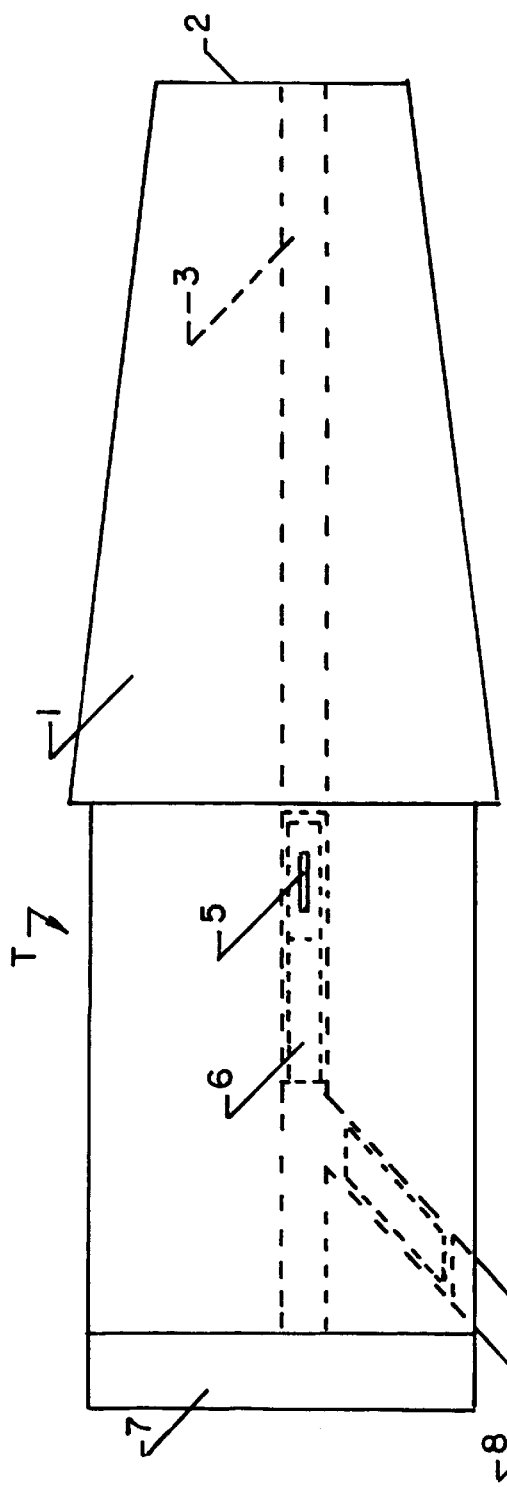
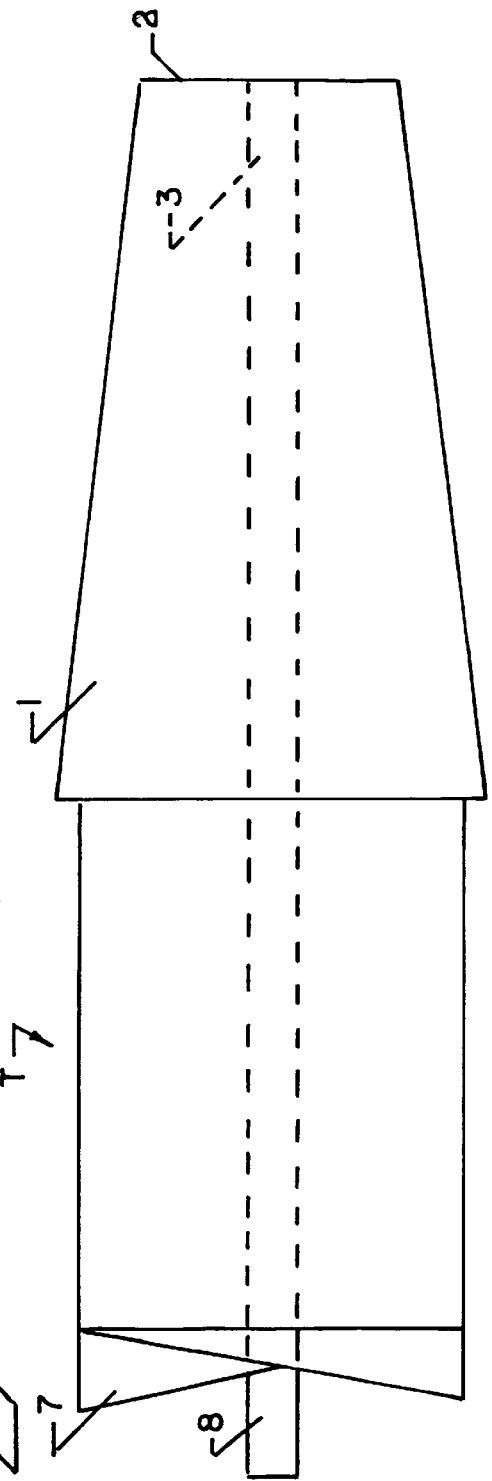

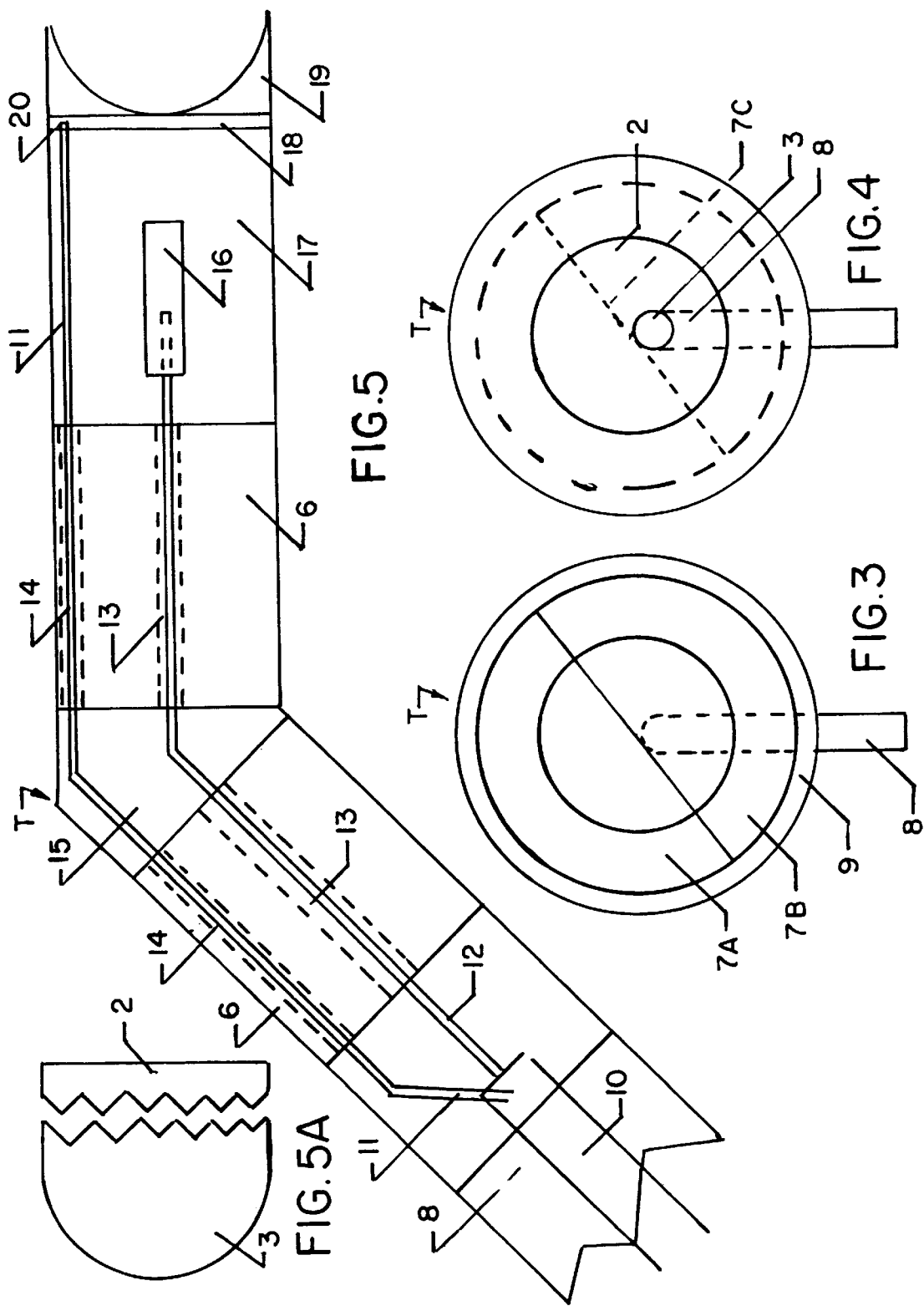

APPARATUS AND METHOD FOR IMPROVED INTRAOCULAR PRESSURE DETERMINATION

FIELD OF INVENTION

The present invention uses a novel applanation tonometer to measure intraocular pressures for the purposes of diagnosing and monitoring treatment for glaucoma. Specifically, the applanation is done with an ultrasonic transducer which measures the corneal thickness at the exact point of applanation. Since applanation pressure is a function of corneal thickness, the simultaneous determination of both allows for more accurate determination of intraocular pressure.

BACKGROUND OF THE INVENTION

Applanation tonometry was popularized by Goldmann as an improved method of intraocular pressure determination in comparison to indentation tonometry. The principal of Goldmann's applanation tonometry is based upon the Imbert-Fick principle, which teaches that the pressure inside a liquid-filled sphere can be determined by measuring the force required to flatten a portion of the surface. It will be obvious to one knowledgeable about the art that variations in thickness of the cornea would affect the accuracy of its applanation in the Goldmann technique. Specifically, a thinner than normal cornea would applanate easier than a normal thickness cornea, thereby generating a falsely low measure of intraocular pressure. Conversely, a thicker cornea than normal would overestimate the true intraocular pressure. Since the diagnosis of glaucoma and the assessment of the adequacy of treatment is largely dependent on intraocular pressure, the accuracy of intraocular pressure measurement is of paramount importance. In order to compensate for variations in corneal thickness, prior art has used pachymetry by optical or ultrasonic means to measure corneal thickness. It is time-consuming and expensive to use a second machine (e.g. ultrasonic pachymetry) sequentially. Moreover, it was impossible to know if the portion of cornea applanated for tonometry was the portion whose thickness was measured. Finally, the determination of both applanation tonometry and corneal pachymetry required solving an equation in order to identify the true intraocular pressure. As a result, the correction of applanation tonometry for corneal thickness variables is not generally done except in research circumstances.

SUMMARY OF THE INVENTION

There exists a need, therefore, for a user-friendly device that can simultaneously determine tonometry and pachymetry, and which can register a more accurate intraocular pressure for general clinical use. The present invention applanates an ultrasonic transducer on the cornea, simultaneously recording applanation pressure and corneal thickness at the exact point of applanation. A microprocessor means converts the applanation pressure to an adjusted intraocular pressure which more accurately reflects the intraocular pressure than by applanation tonometry alone. This device and method allows for quick, convenient, and precise determination of intraocular pressure.

It is an object of the present invention to provide a device which can easily and accurately determine intraocular pressure regardless of variations in corneal thickness.

It is a further object of the present invention to provide pachymetry determination at the exact point of applanation of the cornea.

It is a further object of the present invention to use a microprocessor means to adjust the applanation pressure determination for corneal thickness and to record for the clinician an adjusted intraocular pressure.

Other objects and purposes for this invention will occur to those skilled in the art upon review of the invention as described and analyzed herein, in light of its drawings.

BRIEF DESCRIPTION OF THE DRAWINGS

Referring to the drawings, FIG. 1 discloses the tonometer/pachymeter transducer for providing improved intraocular pressure determination;

FIG. 2 is a top view thereof;

FIG. 3 is a back view thereof;

FIG. 4 is a front view thereof; and

FIG. 5 is a side view of the tonometer/pachymeter transducer association with its signal conveyance rod for providing improved intraocular pressure determination.

DESCRIPTION OF THE PREFERRED EMBODIMENT

It is a preferred embodiment of the present invention to use a solid-state, ultrasonic transducer head working in the 10–50 MHz domain as an applanation surface of predetermined area for contact with the corneal surface.

In another preferred embodiment, the device displays an LED of the applanation pressures, the pachymetry and the (adjusted) intraocular pressure.

EXAMPLE 1

A patient's right eye had undergone photorefractive keratectomy for a minus ten diopters of myopia three months prior to intraocular pressure determination with the present invention. The applanation pressure as measured by a Goldmann tonometer was recorded as 17 mm Hg. The applanation pressure recorded with the present invention was 17 mm Hg. The corneal pachymetry at the applanation location on the cornea was measured as 390 microns, and the corrected intraocular pressure of the present invention was 23 mm Hg. Thus, the present invention demonstrated that the intraocular pressure was higher than would be otherwise be apparent, and most importantly, it was in a range above normal (20 mmHg.).

DESCRIPTION OF DRAWINGS

FIG. 1 is side elevational view of the tonometer/pachymeter transducer of the present invention;

FIG. 2 is a top plan of the tonometer/pachymeter transducer of the present invention;

FIG. 3 is a rear elevational view of the tonometer/pachymerer of the present invention;

FIG. 4 is a front elevational view of the tonometer/pachymeter transducer of the present invention;

FIG. 5 is a side elevational view of the tonometer/pachymeter transducer signal conveyance rod.

The apparatus of this invention describes and shows herein a novel device for simultaneous measurement at the same locus of applanation pressure and of the surface thickness of a fluid-filled sphere for determination of intracavity pressure, wherein a portion or all of the applanating surface is an ultrasonic transducer. The method for utilizing this device includes the simultaneous measurement at the same locus of applanation pressure and of surface thickness of a fluid-filled sphere for determination of intracavity pressure. In addition this novel device provides for simultaneous mesurement at the locus of applanation tonometry and of cornea pachymetry for determination of intraocular pressure, wherein a portion or all of the applanating surface is an ultrasonic transducer.

Finally, this invention includes a method of simultaneous measurement at the same locus of applanation tonometry and of cornea pachymetry for the purpose of intraocular pressure determination. Referring now to the drawings, the tonometer/pachymeter transducer of the present invention is indicated generally by reference figure T. The tonometer/pachymeter includes a transducer body 1 with a corneal contact surface 2. The corneal contact surface 2 creates the optical juncture of the cornea and the transducer body and is used to applanate or flatten a predetermined area of the anterior cornea. This allows the user to view and gauge the position and quality of contact between the cornea and transducer. The transducer body 1 is transparent and allows the user to posteriorly view the corneal contact surface 2. Within body 1 is a signal conveyance rod 3 connected to a transmitter/receiver assembly 4 which is connected to digital readout hardware (not shown) by a coaxial cable 10 housed in a coaxial cable support tube 8. The transmitter/receiver assembly 4 is aimed at the geometric center of the corneal contact surface and projects an ultrasonic signal to the corneal contact surface, through the cornea and collects the return signal from the posterior corneal surface. The ultrasonic signal is propagated from an external source (not shown) and passed to a microprocessor (not shown) through the coaxial cable 10. The microprocessor is programmed to receive the transducer output signal and correct the signal for corneal membrane thickness to determine a true intracavity pressure. Tonometer/pachymeter T also includes an opposing prism assembly 7 which has an upper prism 7A and a lower prism 7B separated by a prism delineation line 7C. The prisms are used to split the image from the corneal contact surface 2 and create a lateral disparity between the prism-induced images. The prisms are parallel to each other and positioned edge to edge and base to apex. The prisms can be orientated from zero to one hundred and eighty degrees on the posterior end of the transducer body 1. Within the body is a solid acrylic insert and wire guide 6. Body 1 also has shoulder 9 so that the tonometer/pachymeter T can be rested in a conventional tonometer mount.

The arrangement of the interior elements of tonometer/pachymeter T are best seen in FIG. 5 and include a shield wire 11 extending from the coaxial cable 10 and also a primary wire 12. The acrylic insert and wire guide 6 includes a drilled hole wire guide 13 for the primary wire 13 and a drilled hole wire guide 14 for the shield wire 11. An air gap 15 is position between the two wire guides. The shield wire 11 is connected to a germanium disc 18 by solder connection 20. A signal emitter 16 is embedded in a graphite casing 17 which is glued or otherwise attached to the germanium disc 18. A silicone concave collar 19 is mated to the posterior end of the signal conveyance rod.

Variations or modifications to the subject matter of this invention may occur to those skilled in the art upon review of the summary provided herein, in addition to the description of its preferred embodiment, in light of the drawings. Such variations, if within the spirit of this invention, are intended to be encompassed within the scope of the invention as described herein.

I claim:

1. An applanation apparatus which allows for the determination of applanation pressure and membrane thickness of a human eye having a fluid filled cavity comprising:

a transparent transducer body having a corneal contact surface for applanation of the cornea; and an ultrasonic transmitter and receiver within said transparent transducer body for sending and receiving an ultrasonic signal to said applanated cornea, said ultrasonic signal processed to determine the applanation pressure and membrane thickness of the human eye.

2. The applanation apparatus of claim 1 including a microprocessor, the microprocessor capable of receiving said ultrasonic signal, said ultrasonic signal being indicative of applanation pressure, said microprocessor capable of correcting said ultrasonic signal for a corneal membrane thickness and to determine a true intracavity pressure independent of corneal membrane thickness.

3. The applanation apparatus of claim 2 wherein said microprocessor determines the membrane thickness at the point of applanation.

4. A method of determining intraocular pressure of a human eye comprising: placing a transducer against a cornea, said transducer including a transparent body and a corneal contact surface for placing against the cornea, an ultrasonic transmitter and receiver within said body, said ultrasonic transmitter being in communications with a microprocessor, said microprocessor being capable of correcting an ultrasonic signal for a corneal membrane thickness and to determine a true intraocular pressure independent of corneal membrane thickness, creating an applanation point on the cornea with said corneal contact surface;

measuring the membrane applanation pressure at said applanation point with said ultrasonic transmitter and receiver; and correcting the measured intracavity pressure for membrane thickness.

5. The applanation apparatus of claim 1 further comprising an opposing prism assembly.

6. The applanation apparatus of claim 2 further comprising a signal conveyance rod between said corneal contact surface and said ultrasonic transmitter and receiver.

7. The applanation apparatus of claim 6, further comprising a signal emitter on said signal conveyance rod.

8. The applanation apparatus of claim 7, further comprising a germanium disc on said signal emitter.

* * * * *